US005747309A

United States Patent [19]
Allan et al.

[11] Patent Number: 5,747,309
[45] Date of Patent: May 5, 1998

[54] BACTERIAL VACCINES USING VACCINE STRAINS OF PATHOGENIC BACTERIA

[75] Inventors: Brenda J. Allan; Andrew A. Potter, both of Saskatoon, Canada

[73] Assignee: University of Saskatchewan, Canada

[21] Appl. No.: 418,520

[22] Filed: Apr. 7, 1995

Related U.S. Application Data

[63] Continuation of Ser. No. 115,683, Sep. 3, 1993, abandoned, which is a continuation-in-part of Ser. No. 939,496, Sep. 4, 1992, abandoned.

[51] Int. Cl.⁶ .................. C12N 15/00; C12N 1/00; C12N 1/20; A61K 39/108
[52] U.S. Cl. .................. 435/172.3; 435/172.1; 435/243; 435/252.8; 424/184.1; 424/234.1; 424/241.1; 424/257.1; 424/93.4
[58] Field of Search .................. 424/184.1, 234.1, 424/241.1, 257.1, 93.4; 435/172.1, 172.3, 243, 252.8

[56] References Cited

U.S. PATENT DOCUMENTS

| | | | |
|---|---|---|---|
| 4,190,495 | 2/1980 | Curtiss | 435/172 |
| 4,404,186 | 9/1983 | Ron et al. | 424/92 |
| 4,888,170 | 12/1989 | Curtiss | 424/93 |
| 5,077,044 | 12/1991 | Stocker | 435/172.3 |
| 5,210,035 | 5/1993 | Stocker | 435/172.3 |
| 5,213,972 | 5/1993 | McCandliss | 435/89 |

FOREIGN PATENT DOCUMENTS

| | | |
|---|---|---|
| WO92/11361 | 7/1991 | WIPO . |
| WO91/15572 | 10/1991 | WIPO . |
| WO92/12732 | 8/1992 | WIPO . |

OTHER PUBLICATIONS

Allan et al 1993. Poster Abstract. Proceedings 42nd Western Poultry Disease Conference. p. 87.
Allan et al. 1993. Canadian J. Vet. Res. 57:146–151.
Lafont et al. 1984. Avian Dis. 28(4):1016–1025.
Ernst et al. 1978. Constitutive Expression of the Iron Enterachelin and Ferrichrome . . . J. Bacteriol. 135(3): 928–34.
Wilson et al 1990. Alternative Methods of Alternating Salmonella . . . Res. Microbiol. 141:827–830.
Aitken et al., "Recombinant enterotoxins as vaccines against *Escherichia coli*–induced diarrhea", *Conf. Abst.—Vaccine,* vol. 10, Iss. 4, pp. 270 (1990).
Bagg et al., "Mapping of a Mutation Affecting Regulation of Iron Uptake System in *Escherichia coli* K–12", *J. of Bacteriology.,* vol. 161, pp. 450–453 (1985).
Bender et al., "Tn10 insertion specificity is strongly dependent upon sequences immediately adjacent to the target–site consensus sequence", *Proc. Natl. Acad. Sci. USA,* vol. 89, pp. 7996–8000 (1992).
Bochner et al., "Positive Selection for Loss of Tetracycline Resistance", *J. of Bacteriology,* vol. 143, No. 2, pp. 926–933 (1980).

Bouvier et al., "Multiple regulatory signals in the control region of the *Escherichia coli* carAB operon", *Proc. Natl. Acad. Sci. USA,* vol. 81, pp. 4139–4143 (1984).
Calderwood et al., "Iron Regulation of Shiga–Like Toxin Expression in *Escherichia coli* is Mediated by the fur Locus", *J. of Bacteriology,* vol. 169, No. 10, pp. 4759–4764 (1987).
Charles et al., "Gene expression and the development of live enteric vaccines", *Tibtech,* vol. 8, pp. 117–121 (1990).
Cheville et al., "Comparative Pathologic Findings of *Escherichia coli* Infection in Birds", *JAVMA,* vol. 173, No. 8, pp. 584–589 (1978).
Cooper et al., "Vaccination of chickens with a *Salmonella enteritidis* aroA live oral salmonella vaccine", *Microbial Pathogenesis,* vol. 9, pp. 255–265 (1990).
Curtiss, III et al., "*Salmonella typhimurium* Deletion Mutants Lacking Adenylate Cyclase and Cyclic AMP Receptor Protein are Avirulent and Immunogenic", *Infection and Immunity,* vol. 55, No. 12, pp. 3035–3043 (1987).
Davies et al., "Genetics of Resistance to Colicins in *Escherichia coli* K–12: Cross–Resistance Among Colicins of Group A", *J.of Bacteriology,* vol. 123, pp. 102–117 (1975).
Delaney et al., "Isolation and Characterization of the *Escherichia coli* htrD Gene, Whose Product is Required for Growth at High Temperatures", *J. of Bacteriology,* vol. 174, No. 4, pp. 1240–1247 (1992).
Dozois et al., "pap–and pil–Related DNA Sequences and Other Virulence Determinants Associated with *Escherichia coli* Isolated from Septicemic Chickens and Turkeys", *Infection and Immunity,* vol. 60, No. 7, pp. 2648–2656 (1992).
Emery et al., "Development of a Temperature Sensitive Mutant of *E. coli* for The Control of Colibacillosis in Turkeys", *39th North Central Avian Dis. Conf.,* pp. 32–34 (1988).
Fairweather et al., "Use of Live Attenuated Bacteria To Stimulate Immunity", *Res. Microbiol.,* vol. 141, pp. 769–773 (1990).
Fields et al., "Mutants of *Salmonella typhimurium* that cannot survive within the macrophage are avirulent", *Proc. Natl. Acad. Sci. USA,* vol. 83, pp. 5189–5193 (1986).

(List continued on next page.)

*Primary Examiner*—Nita Minnifield
*Attorney, Agent, or Firm*—Burns, Doane, Swecker & Mathis L.L.P.

[57] ABSTRACT

Vaccines are provided for vaccinating an animal against pathogenic bacteria, including *E. coli*. The invention also encompasses methods of preparing and methods of use of vaccine strains and compositions that result from or are used in these methods. In particular, pathogenic bacteria comprising at least one attenuating mutation selected from the group consisting of a pyrimidine pathway mutation, an iron metabolism mutation, and a colicin transport mutation which retain their immunogenicity so as to provide protective immunity are provided.

83 Claims, No Drawings

OTHER PUBLICATIONS

Fontaine et al., "Construction And Evaluation Of Live Attenuated Vaccine Strains Of *Shigella flexineri* And *Shigella dysenteriae*", *Res. Microbiol.*, vol. 141, pp. 907–912 (1990).

Foster et al., "Effect of *Salmonella typhimurium* Ferric Uptake Regulator (fur) Mutations on Iron–and pH–Regulated Protein Synthesis", *J. of Bacteriology*, vol. 174, pp. 4317–4323 (1992).

Francis et al., "Evaluation of a live avirulent *Escherichia coli* vaccine for K88+, LT+ enterotoxigenic colibacillosis in weaned pigs", *Am. J. Vet. Res.*, vol. 52, No. 7, pp. 1051–1055 (1991).

Gatenby et al., "Chaperonin assisted polypeptide folding and assembly: implications for the production of functional proteins in bacteria", *Tibtech*, vol. 8 pp. 354–357 (1990).

Gilligan et al., "Oral Enteric Vaccines—Clinical Trials", *J. of Clin. Phar. and Therapeutics*, vol. 16, pp. 309–335 (1991).

Griffin et al., "Construction of an aroA mutant of *Salmonella* serotype Gallinarum: its effectiveness in immunization against experimental fowl typhoid", *Vaccine*, vol. 11, Issue 4, pp. 457–462 (1993).

Griggs et al., "Mechanism for Iron–Regulated Transcription of the *Escherichia coli* cir Gene: Metal–Dependent Binding of Fur Protein to the Promoters", *J. of Bacteriology*, vol. 171, pp. 1048–1054 (1989).

Gross et al., "Colibacillosis", Diseases of Poultry, *Iowa State University Press*, 9th Edition, pp. 138–144 (1991).

Halling et al., "DNA sequence organization of IS10–right of Tn10 and comparison with IS10–left", *Proc. Natl. Acad. Sci. USA*, vol. 79, pp. 2608–2612 (1982).

Hantke et al., "Cloning of the repressor protein gene of iron–regulated systems in *Escherichia coli* K12", *Mol. Gen. Genet.*, vol. 197, pp. 337–341 (1984).

Hantke, "Negative control of iron uptake systems in *Escherichia coli*", *FEMS Microbiology Letters* 15, pp. 83–86 (1982).

Hantke, "Regulation of Ferric Iron Transport in *Escherichia coli* K12: Isolation of a Constitutive Mutant", *Mol. Gen. Genet.*, vol. 182, pp. 288–292 (1981).

Hassan et al., "Prevention of colonization by invasive *Salmonella typhimurium* by oral immunization of white leghorn chicks with an avirulent Δ cya Δ crp *S. typhimurium* vaccine strain", *71st Annual Meeting of the Conference of Research Workers in Animal Disease*, p. 8, Abst. 42 (1990).

Hessemann et al., "Iron uptake and virulence of *Yersinia enterocolitica*", *93rd Gen. Mtg. of the ASM*, Session 277, Abst. B–295 (1993).

Hiraga et al., Chromosome Partitioning in *Escherichia coli*: Novel Mutants Producing Anucleate Cells, *J. of Bacteriology*, vol. 171, pp. 1496–1505 (1989).

Hormaeche et al., "Immunity Induced By Live Attenuated *Salmonella* Vaccines", *Res. Microbiol.*, vol. 141, pp. 757–764 (1990).

Jenness et al., "pyrB Mutations as Suppressors of Arginine Auxotrophy in *Salmonella typhymurium*", *J. Bacteriology*, vol. 141, pp. 33–40 (1980).

Jones et al., "Vaccination of calves agianst salmonellosis with a double aro mutant of *S. typhimurium*", *Conf. Abst.—Vaccine*, vol. 10, Iss. 4, pp. 280 (1992).

Karow et al., Isolation and Characterization of the *Escherichia coli* htrB Gene, Whose Product is Essential for Bacterial Viability above 33° C. in Rich Media, *J. of Bacteriology*, vol. 173, No. 2, pp. 741–750 (1991).

Karow et al., "Sequencing, mutational analysis and transcriptional regulation of the *Escherichia coli* htr B gene", *Molecular Microbiol.*, vol. 5(9), pp. 2285–2292 (1991).

Karow et al., "Complex phenotypes of null mutations in the htr genes, whose products are essential for *Escherichia coli* growth at elevated temperatures", *Res. Microbiol.*, vol. 142, pp. 289–294 (1991).

Kleckner et al., "DNA Sequence Analysis of Tn10 Insertions: Origin and Role of 9 bp Flanking Repetitions during Tn10 Translocation", *Cell*, vol. 16, 711–720 (1979).

Kleckner et al., "Transposon Tn 10", Mobile DNA, *Am. Soc. for Microbiol.*, pp. 227–268 (1989).

Kleckner et al., "Use of Transposons with Emphasis on Tn10", *Methods in Enzymology*, vol. 204, pp. 139–180 (1991).

Kotloff et al., "Safety, Immunogenicity, and Efficacy in Monkeys and Humans of Invasive *Escherichia coli* K–12 Hybrid Vaccine Candidates Expressing *Shigella flexneri* 2a Somatic Antigen", *Infection and Immunity*, vol. 60, No. 6, pp. 2218–2224 (1992).

Kunkel et al., "Rapid and efficient site–specific mutagenesis without phenotypic selection", *Proc. Natl. Acad. Sci. USA*, vol. 82, pp. 488–492 (1985).

Lafont et al., "Presence and Expression of Aerobactin Genes in Virulent Avian Strains of *Escherichia coli*", *Infection and Immunity*, vol. 55, No. 1, pp. 193–197 (1987).

LaRossa et al., "Physiological roles of the DnaK and GroE stress proteins: catalysts of protein folding or macromolecular sponges?", *Molecular Microbiol.*, vol. 5(3), pp. 529–534 (1991).

Leitner et al., Colonization of *Escherichia coli* in Young Turkeys and Chickens, *Avian Diseases*, vol. 36, pp. 211–220 (1992).

Leung et al., "Tn5–Induced Protease–Deficient Strains of *Aeromonas hydrophila* with Reduced Virulence for Fish", *Infection and Immunity*, vol. 56, No. 10, pp. 2639–2644 (1988).

Levin et al., "Regulation of aspartate transcarbamoylase synthesis in *Escherichia coli*: Analysis of deletion mutations in the promoter region of the pyrBI operon", *Proc. Natl. Acad. Sci. USA*, vol. 82, pp. 4643–4647 (1985).

Leyh et al., "Transposon mutagenesis in *Bordetella avium*", *Am. J Vet Res*, vol. 49, No. 5, pp. 687–692 (1988).

Lipinska et al., "Identification, Characterization, and Mapping of the *Escherichia coli* htrA Gene, Whose Product Is Essential for Bacterial Growth Only at Elevated Temperatures", *J. of Bacteriology*, vol. 171, No. 3, pp. 1574–1584 (1989).

Maloy et al., "Selection for Loss of Tetracycline Resistance by *Escherichia coli*", *J. of Bacteriology*, vol. 145, No. 2, pp. 1110–1112 (1981).

Meister et al., "Mechanism and Regulation of The Glutamine–Dependent Carbamyl Phosphate Synthetase of *Escherichia coli*", *Advances In Enzymology*, vol. 62, pp. 315–374 (1989).

Melamed et al., "A Vaccine Against Avian Colibacillosis Based on Ultrasonic Inactivation of *Escherichia coli*", *Avian Diseases*, vol. 35, pp. 17–22 (1991).

Mergeay et al., "Physiology and Genetics of Carbamoylphosphate Synthesis in *Escherichia coli* K12", *Molec. Gen. Genet.*, vol. 133, pp. 299–316 (1974).

Miller et al., "General Microbiology of recA: Environmental and Evolutionary Significance", *Annu. Rev. Microbiol.*, vol. 44, pp. 365–394 (1990).

Miller et al., "Salmonella Vaccines With Mutations In The phoP Virulence Regulon", *Res. Microbiol.*, vol. 141, pp. 817–821 (1990).

Moon et al., "Session 7: *Escherichia coli*—Vaccines for preventing enterotoxigenic *Escherichia coli* infections in farm animals", *Conf. Abst.—Vaccine*, vol. 10, Iss. 4, pp. 269–270 (1990).

Nakumura et al., "Pathology of Spontaneous Colibacillosis in a Broiler Flock", *Vet. Pathol.*, vol. 22, pp. 592–597 (1985).

Niederhoffer et al., "Control of *Escherichia coli* Superoxide Dismutase (sodA and sodB) Genes by the Ferric Uptake Regulation (fur) Locus", *J. of Bacteriology*, vol. 172, No. 4, pp. 1930–1938 (1990).

Neidhardt et al., "Molecular Cloning and Expression of a Gene That Controls the High-Temperature Regulon of *Escherichia coli*", *J. of Bacteriology*, vol. 153, No. 2, pp. 597–603 (1983).

Nyunoya et al., "The carB gene of *Escherichia coli*: A duplicated gene coding for the large subunit of carbamoyl–phosphate synthetase", *Proc. Natl. Acad. Sci., USA*, vol. 80, pp. 4629–4633 (1983).

Nyunoya et al., "Sequence of the Small Subunit of Yeast Carbamyl Phosphate Synthetase and Identification of Its Catalytic Domain", *J. of Biological Chemistry*, vol. 259, No. 15, pp. 9790–9798 (1984).

O'Hanley, "Vaccines Against *Escherichia coli* Urinary Tract Infections", *New Generation Vaccines, Marcel Dekker, Inc.*, pp. 631–665 (1990).

Piette et al., "DNA sequence of the carA gene and the control region of carAB: Tandem promoters, respectively controlled by arginine and the pyrimidines, regulate the synthesis of carbamoyl–phosphate synthetase in *Escherichia coli* K–12", *Proc. Natl. Acad. Sci. USA*, vol. 81, pp. 4134–4138 (1984).

Raina et al., "A New *Escherichia coli* Heat Shock Gene htrC, Whose Product Is Essential for Viability Only at High Temperatures", *J. of Bacteriology*, vol. 172, No. 6, pp. 3417–3426 (1990).

Raina et al., "The *Escherichia coli* htr P Gene Product Is Essential for Bacterial Growth at High Temperatures: Mapping, Cloning, Sequencing, and Transcriptional Regulation of htr P", *J. of Bacteriology*, vol. 173, No. 19, pp. 5999–6008 (1991).

Rioux et al., "Colorimetric Determination of Catechol Siderophores in Microbial Cultures", *Analytical Biochemistry*, vol. 133, pp. 163–169 (1983).

Sambrook et al., *Molecular Cloning*, 2nd Edition 1.5, 1.68–1.71, 1.74, 1.75, and 9.34–9.55 (1989).

Stauffer et al., "Construction and expression of hybrid plasmids containing the *Escherichia coli* gly A gene", *Gene*, vol. 14, pp. 63–72 (1981).

Sternberg et al., "Bacteriophage–Mediated Generalized Transduction in *Escherichia coli* and *Salmonella typhimurium*", *Methods in Enzymology*, vol. 204, pp. 18–29 (1991).

Tardat et al., "Iron and oxygen regulation of *Escherichia coli* MnSOD expression: competition between the global regulators Fur and ArcA for binding to DNA", *Molecular Microbiology*, vol. 9(1), pp. 53–63 (1993).

Trotta et al., "Reversible Dissociation of Carbamyl Phosphate Synthetase into a Regulated Synthesis Subunit and a Subunit Required for Glutamine Utilization", *Proc. Natl. Acad. Sci., USA*, vol. 68, No. 10, pp. 2599–2603 (1971).

Van Den Hurk, et al., "Quantitation of Hemorragic Enteritis Virus Antigen and Antibody Using Enzyme–Linked Immunosorbent Assays", *Avian Diseases*, vol. 30, No. 4, pp. 662–671 (1986).

Van Den Hurk, et al., "Efficacy of Avirulent Hemorrhagic Enteritis Virus Propagated in Turkey Leukocyte Cultures for Vaccination against Hemorrhagic Enteritis in Turkeys", *Avian Diseases*, vol. 34, pp. 26–35 (1990).

Vidotto et al., "Virulence Factors of Avian *Escherichia coli*", *Avian Diseases*, vol. 34, pp. 531–538 (1990).

Wandersman et al., "TolC, an *Escherichia coli* outer membrane protein required for hemolysin secretion", *Proc. Natl. Acad. Sci. USA*, vol. 87, pp. 4776–4780 (1990).

Webster, "The tol gene products and the import of macromolecules into *Escherichia coli*", *Molecular Microbiology*, vol. 5(5), pp. 1005–1011 (1991).

Whittam et al., "Genetic Relationships among Pathogenic Stains of Avian *Escherichia coli*"*Inf. Immun.*, 56:2458–2466 (1988).

World Health Organization Meeting Report, "Potential use of live viral and bacterial vectors for vaccines", *Vaccine*, vol. 8, pp. 425–437 (1990).

BACTERIAL VACCINES USING VACCINE STRAINS OF PATHOGENIC BACTERIA

CROSS-REFERENCE TO RELATED APPLICATIONS

This application is a continuation of U.S. patent application Ser. No. 08/115,683, filed Sep. 3, 1993, now abandoned, which is a continuation-in-part of U.S. patent application Ser. No. 07/939,496, filed Sep. 4, 1992, now abandoned, which are herein incorporated by reference in their entirety.

FIELD OF THE INVENTION

The present invention relates to vaccines against pathogenic bacteria.

References

The following references are cited in this application as superscript numbers at the relevant portions of the application.

1. Aitken et al., Vaccine, 10:271 (1992).
2. Bouvier et al., Proc. Nat'l. Acad. Sci. USA, 81:4139–4143 (1984).
3. Cheville et al., J. Am. Vet. Med. Assoc., 173:584–587 (1978).
4. Dozois et al., Infection and Immunity, July 1992:2648–2656 (1992).
5. Fairweather et al., Res. Microbiol., 141:769–773 (1990).
6. Fontaine et al., Res. Microbiol., 141:907–912 (1990).
7. Gross, Diseases of Poultry, 9th Ed.:138–144 (1991).
8. Curtiss III et al., Infection and Immunity, 55:3035–3043 (1987).
9. Hormaeche et al., Res. Microbiol., 141:757–764 (1990).
10. Jones et al., Vaccine, 10:280 (1992).
11. Lafont et al., Infection and Immunity, Jan. 1987:193–197 (1987).
12. Leitner et al., Avian Dis., 36:211–220 (1992).
13. Meister, Adv. Enz., 62:315–374 (1989).
14. Mergeay et al., Molec. Gen. Genet., 133:299–316 (1974).
15. Miller et al., Res. Microbiol., 141:817–821 (1990).
16. Moon, Vaccine, 10:269 (1992).
17. Nakamura et al., Vet. Pathol., 2:592–597 (1985).
18. Nyunoya et al., Proc. Nat'l. Acad. Sci. USA, 80:4629–4633 (1983).
19. Nyunoya et al., J. Biol. Chem., 259:9790–9798 (1984).
20. Piette et al., Proc. Nat'l. Acad. Sci. USA, 81:4134–4138 (1984).
21. Sternberg et al., Methods Enz., 204:18–28 (1991).
22. Stocker, U.S. Pat. No. 5,077,044 (1991).
23. Trotta et al., Proc. Nat. Acad. Sci. USA, 68:2599–2603 (1971).
24. Vidotto et al., Avian Dis., 34:531–538 (1990).
25. Ron, U.S. Pat. No. 4,404,186 (1983).
26. Kunkel, Proc. Nat'l. Acad. Sci. USA, 82:488–492 (1985).
27. Sambrook et al., Molecular Cloning, 2nd Ed.:1.5, 1.74 and 1.75 (1989).
28. Stocker, U.S. Pat. No. 5,210,035 (1993).
29. Emery et al., North Central Avian Diseased Conference, 23–34 (1988).
30. Griffin et al., Vaccine, 11:457–462(1993).
31. Nagaraja et al., International Publication No. WO92/12732 (1992).
32. Bagg et al., J. Bact., 161:457–462 (1993).
33. Hantke, FEMS Micro. Letters, 15:83–86 (1982).
34. Hantke, Mol. Gen. Genet., 182:288–292 (1991).
35. Webster, Mol. Microbiol., 5:1005–1011 (1991).
36. Wandersman et al., Proc. Nat'l. Acad. Sci. USA, 87:4776–4780 (1990).
37. Davies et al., J. Bact., 123:102–117 (1975).
38. Leyh et al., Am. J. Vet. Res., 49:687–692 (1988).
39. Heesemann et al., 93rd Gen. Mtg. of A.S.M., Abstract B-295 (1993).
40. Rioux et al., Anal. Biochem., 133:163–169 (1983).
41. Fields et al., Proc. Nat'l. Acad. Sci. USA, 83:5189–5193 (1986).
42. Kleckner, Cell, 16:711–720 (1979).
43. Halling et al., Proc. Nat'l. Acad. Sci. USA, 79:2608–2612 (1982).
44. Bender et al., Proc. Nat'l. Acad. Sci. USA, 89:7996–8000 (1992).

The disclosures of the above publications and patents are herein incorporated by reference in their entirety to the same extent as if the language of each individual publication or patent were specifically and individually included herein.

BACKGROUND OF THE INVENTION

Vaccination with live attenuated strains is extensively and successfully used in the prevention of various viral diseases of man, such as polio and smallpox. However, there are only a few such vaccines effective against bacterial diseases of man or domestic animals; BCG vaccine for prevention of tuberculosis, strain 19 vaccine against bovine brucellosis and Sterne's spore vaccine against anthrax in cattle are well-known examples.

Use of live vaccines is hampered by a number of factors. Some strains considered for use as live vaccines retain an unacceptable degree of virulence, by reversion or otherwise. Some live vaccines display short persistence of immunity attributed to early disappearance of the vaccine strain from host tissues and, in some instances, incomplete immunity so that some vaccinated animals die after challenge with a virulent strain.

The non-virulent strains used as vaccines have been obtained in various ways. The BCG strain was derived by empirical procedures during prolonged in vitro cultivation, and probably owes its non-virulence to multiple unidentified mutations. Sterne's Bacillus anthracis spore vaccine is a strain which has lost the ability to synthesize the polypeptide capsule, important as a determinant of virulence but not as a "protective" antigen. Some experimenters have used as live vaccine merely a sublethal dose of a "wild" strain of relatively low virulence in the sense that the LD50 was a large number of bacteria—a situation in which there is evident risk of severe or fatal infection developing in some vaccinated subjects and of transmission to other hosts.

Since live vaccines have substantially greater probability of success in providing protection for the host against a subsequent invasion of a virulent wild strain than killed vaccines or subunit vaccines, it is desirable to develop new live vaccines which avoid the shortcomings of vaccines prepared previously. Because the immune response of the vertebrate host to antigens, in particular surface antigens, of the pathogenic microorganism is the basic mechanism of protection by vaccination, a live vaccine should retain the antigenic complement of the wildtype strain. The live vaccine should be non-virulent and substantially incapable of sustained multiplication in the host.

Several live attenuated Salmonella vaccines have recently been developed for intracellular pathogenic Salmonella. These include mutant aroA strains[9,10], strains with mutations in the phoP virulence region[5], ΔcyaΔcrp S. typhimurium[8], and aroAaroC mutants[5]. Purine mutations were found to be too attenuating for immunogenicity[5]. An aroA mutant was found to be ineffective against oral challenge when administered orally[30].

Live attenuated vaccine strains of the intracellular pathogenic bacterial *Shigella flexneri* and *S. dysenteriae* have also been developed[6]. For example, novel non-reverting Shigella live vaccines prepared by producing auxotrophic mutants of a pathogenic strain are disclosed in U.S. Pat. No. 5,077,044[22,28].

Vaccines developed for preventing *Escherichia coli* (hereinafter *E. coli*) infections include parenterally administered vaccines containing pilus antigens[16], and orally administered vaccines containing recombinant enterotoxins[1]. Live vaccines using mutant non-pathogenic strains of *E. coli* have also been disclosed[25] A temperature sensitive mutant *E. coli* produced using a chemical mutagen has been administered intravenously and orally[29,31].

*E. coli* infection in turkeys and chickens is manifested in several forms, the most common being colisepticemia, a respiratory disease characterized by airsacculitis, pericarditis, and perihepatitis[7]. This disease is the leading cause of economic losses due to infectious disease to turkey producers in Canada and the United States of America. The primary site of colonization is the upper respiratory tract followed by extension into the lower respiratory tract. *E. coli* is generally inhaled by a contaminated litter dust and subsequently enters the bloodstream, probably via pulmonary lymphatics. Circulating bacteria are then trapped in sinusoids adjacent the central vein of the liver and in the marginal zones of periarteriolar reticular sheaths of the spleen. Such infections frequently develop as a secondary event subsequent to mycoplasma or viral infection. The most common primary viral agents are Newcastle disease virus and hemorrhagic enteritis virus (HEV). Thus, in order to be effective, a vaccine for *E. coli* should be proactive for such secondary infections as well as against primary challenge.

*E. coli* are commonly found in poultry houses. However, only certain isolates are able to cause disease, and these can be grouped by a technique called serotyping. The most common serotypes associated with disease in Canada and the United States of America are 01, 02 and 078[3,17]. Each serotype produces a number of virulence determinants which have been shown to induce protective immunity when incorporated in experimental vaccines. These include fimbriae (pili), appendages used by the bacteria to attach to host tissue, outer membrane proteins which are produced specifically to bind and use host nutrients for their growth, and toxins capable of impairing immune function. However, the delivery of these as vaccine components is usually by injection, a procedure not feasible in the field.

Studies of virulence determinants associated with *E. coli* isolated from colisepticemic chickens and turkeys showed that the presence of the aerobactin system, presence of adherence pili, and resistance to normal serum were associated with *E. coli* causing colisepticemia (in poultry) or lethality (in day-old chicks )[4,24]. Other characteristics present in virulent strains were invasion for HeLa and chicken fibroblast cells and colicin V[24].

Despite advances in the field, there still exists a need for an effective, easily administered vaccine against infections from pathogenic bacteria, including *E. coli*.

SUMMARY OF THE INVENTION

Vaccines are provided for vaccinating an animal against pathogenic bacteria, including *E. coli*. The invention also encompasses methods of preparing and methods of use of vaccine strains and compositions that result from or are used in these methods.

Accordingly, in one aspect the invention provides vaccine strains of pathogenic bacteria comprising at least one mutation selected from the group consisting of a pyrimidine pathway mutation, an iron metabolism mutation, and a colicin transport mutation, said mutation providing attenuation of the virulence of said bacteria.

Another aspect of the invention provides a method of preparing a vaccine strain of a pathogenic bacteria comprising producing at least one mutation selected from the group consisting of a pyrimidine pathway mutation, an iron metabolism mutation, and a colicin transport mutation in a virulent strain of said pathogenic bacteria to provide an attenuated organism; isolating the attenuated organism; and using it as a vaccine strain.

A further aspect of the invention provides a composition comprising at least one vaccine strain of a pathogenic bacteria comprising at least one attenuating mutation selected from the group consisting of a pyrimidine pathway mutation, an iron metabolism mutation and a colicin transport mutation.

Yet another aspect of the invention is a method for preventing a bacterial disease in an animal comprising administering to the animal to be protected an effective amount of at least one vaccine strain of a pathogenic bacteria comprising at least one mutation selected from the group consisting of a pyrimidine pathway mutation, an iron metabolism mutation, and a colicin transport mutation.

DESCRIPTION OF THE INVENTION

A. Definitions

As used herein the following terms have the following meanings:

Antigen: refers to a molecule containing one or more epitopes that will stimulate a host's immune system to make a humoral and/or cellular antigen-specific response. For the purposes of this application, "antigen" and "immunogen" are used interchangeably.

Attenuation: diminution of virulence in a strain of an organism.

Bacterial disease: a disease caused by a bacteria, including those diseases which occur only in the presence of a predisposing viral infection or when the host is under stress.

carAB: the operon which codes for carbamoyl phosphatase. When used in [] following a serotype number, it denotes the presence of a carAB mutation in that organism.

Colicin transport mutation: a mutation of one or more of the genes coding for proteins involved in the recognition and/or transport of macromolecules, as exemplified by colicin, into a bacterial cell.

Colisepticemia: disease caused by *E. coli* infection, including, but not limited to, cellulitis, airsaculitis and omphalitis. For the purposes of this application, "colisepticemia" and "colibacillosis" are used interchangeably.

Effective amount: dose required to induce an immune response sufficient to protect an animal against disease.

Extracellular pathogenic bacteria: a pathogenic bacteria which does not need to replicate within a host cell to cause disease.

fur: the gene which codes for the fur protein that functions as a global regulator in bacterial cells. When used in [] following a serotype number, it denotes the presence of a fur mutation in that organism.

Immune response: development in the host of a cellular and/or antibody-mediated immune response to a composition or vaccine of interest. Such a response usually consists of the subject producing antibodies, B cells, helper T cells, suppressor T cells, and/or cytotoxic T cells directed specifically to an antigen or antigens included in the composition or vaccine of interest.

Immunogenic: capable of inducing an immune response.

Intracellular pathogenic bacteria: a pathogenic bacteria which must replicate within a host cell to cause disease.

Iron metabolism mutation: a mutation of one or more of the genes coding for proteins involved in iron uptake, utilization, and/or regulation in a bacterial cell. For the purposes of this application, iron metabolism mutation includes modifications to any metabolic function regulated by one of these genes, whether or not this function is related to iron.

Morbidity: evidencing disease, including the presence of lesions in tissues.

Pathogenic: capable of causing disease.

Protective: capable of protecting an animal against disease.

Pyrimidine pathway mutation: a mutation of one or more of the genes coding for an enzyme involved in the pyrimidine pathway of a bacterial cell.

Stable mutant: a mutant with a low frequency of reversions. In general, mutants with reversion frequencies less than about $10^{-7}$ are considered stable, with reversion frequencies less than $1 \times 10^{-8}$ considered safe for vaccine strains.

tolC: the gene which codes for an outer membrane protein that is involved in colicin transport, hemolysin transport, and processing of other membrane proteins as well as partitioning of the chromosome. When used in [] following a serotype number, it denotes the presence of a tolC mutation in that organism.

Transduction: transfer of genetic material and its phenotypic expression from one cell to another by viral infection.

Vaccine strain: a normally virulent strain of bacteria which has been attenuated so that it no longer causes disease in the host, yet has the ability to induce an immune response in the host to protect the host from a virulent pathogenic strain. Vaccine strains may be live or killed. Killed vaccine strains may be preferred for in ovo inoculation or parenteral administration; live vaccine strains may be preferred for other forms of administration.

Virulent: capable of producing disease.

DETAILED DESCRIPTION OF THE INVENTION

This invention provides vaccine strains of attenuated pathogenic bacteria. Preferred vaccine strains of this invention are mutants that have deletions, since these mutants should not revert. Particularly preferred vaccine strains of this invention include auxotrophic mutants having a pyrimidine pathway mutation causing a requirement in the strain for uracil, for example carAB, pyrB, pyrc, pyrD and pyrE. Also particularly preferred vaccine strains of this invention include mutants defective in iron metabolism, for example, fur, fhuA (or tonA), fepA, cir and tonB. Additional particularly preferred vaccine strains of the present invention include mutants with mutations in the colicin transport mechanism, for example tolC, tolQ, tolR, tolA, tolB, and tolZ. Most preferred live vaccine strains of this invention are auxotrophic mutants having a mutant carAB operon causing a requirement in the strains for both arginine and uracil. Also most preferred are mutants having a fur mutation which causes reduced synthesis of a protein involved in regulation of iron intake. Also most particularly preferred are mutants having a tolC mutation which prevents trans-location of colicins and appears to be required for hemolysin secretion[36]. Thus, the live vaccine strains of this invention, when introduced into the host, will continue to live and elicit a protective immune response, but will be unable to cause disease.

The use of a live vaccine strain having a mutation such that the bacterial strain requires the provision of more than one nutrient requirement reduces the chance that the host might inadvertently provide the necessary metabolites for replication of the bacteria. Introduction of a second auxotrophic or other mutation into the live vaccine strain will further reduce the chance of reversion to wildtype.

It has been unexpected and surprising to find that pathogenic bacteria containing mutations in the pyrimidine pathway would be useful as live vaccine strains, in view of the fact that purine mutants were previously found to be too attenuated to be immunogenic . It is likewise unexpected that mutations in the iron metabolism pathway would cause attenuation of pathogenic bacteria so as to make them useful in the vaccine strains of the present invention. Similarly, it is unexpected that colicin tolerant mutants would be attenuated. Thus, by applying the basic aspects of this invention as set forth herein, one skilled in the art will recognize the broad applicability of the present invention.

The methods of this invention for preparing vaccines, as well as the vaccines of this invention, have a large number of advantages over prior methods and vaccines. As contrasted with other vaccines, the subject invention provides for the exact cause of the loss of virulence. The subject strains should be able to persist in the host for extended periods of time, usually weeks, to enhance the effectiveness of the immunizing effect by continuous stimulation of the host immune system until the host immune system has cleared all the organisms. In view of the fact that the non-virulence does not depend on any host cellular function, the subject strains are expected to be non-virulent even in immunodeficient hosts.

The vaccines of this invention may be used with a wide variety of animals, as well as man. This includes fish, birds, reptiles, avian species, and mammals. More particularly included are domestic animals which are treated by vaccines today or could be treated if susceptible to bacterial diseases, such as avian, leporine, bovine, porcine, equine, caprine, ovine or other animal species.

The mechanism and regulation of carbamoyl phosphate synthetase in *E. coli* has been extensively studied for many years[2,13,23]. This enzyme catalyzes the first reaction in pyrimidine and arginine biosynthesis, and is the product of the carAB operon. Numerous mutations of the carAB operon are known, some of which make *E. coli* not strictly auxotrophic for arginine and uracil[14]. The sequence of the two portions of the carAB operon, the carA gene and the carB gene are described in the literature[18,19,20].

The mechanism and regulation of ferric iron transport in *E. coli* and *Salmonella typhimurium* has been studied[32-34]. Mutants defective in iron metabolism are constitutively derepressed for the synthesis of siderophores and their receptors. Recent studies of fur mutants in Yersinia showed that fur mutation had no effect on virulence[39]. Thus, it was unexpected to find that the fur mutants of the present inventions were attenuated.

The mechanism and regulation of macromolecule import into *E. coli* has been extensively studied for many years[35-37]. Bacteria carrying specific mutations which prevent binding of colicins have been termed colicin resistant. Mutations which allow normal binding of colicins, but do not allow translocation of the macromolecules to their target have been designated colicin tolerant (tol). Numerous colicin resistant and colicin tolerant mutants are known[37].

The particular mutation, for example the pyrimidine pathway mutation, the iron metabolism mutation, or the colicin transport mutation, may be introduced into pathogenic bacteria by means of conjugation, transformation, and/or phage-mediated transduction[21,27]. The particular method of introduction is not critical, and the preferred method may depend on the organism being transduced and the particular mutation to be introduced. These operons may be incorporated into many bacteria. This includes gram positive bacteria such as Streptomyces and Bacillus species. In particular, they may be introduced into any gram negative bacteria, and Escherichia, Pseudomonas, Salmonella, Shigella and Yersinia species are expected to be particularly useful in the present invention.

After transducing the pathogenic bacteria with the mutation, they are grown under conditions facilitating isolation of the mutants, either under conditions under which such mutants have a selective advantage over parental bacteria or under conditions allowing their easy recognition from unaltered bacteria or mutants of other types. The isolated mutants are cloned and screened for lack of virulence and ability to induce an immune response in a host to protect the host from a virulent pathogenic strain.

Among bacteria, the subject invention is particularly applicable to a wide variety of E. coli strains, more particularly serotypes 01, 02 and 078. Other pathogenic bacteria for which the subject invention may also be employed include, for example, Streptomyces, Bacillus, Salmonella, Shigella, Yersinia, Mycoplasma, Chlamydia, Streptococcus and Staphylococcus species.

We have found that certain additional criteria may be used in selecting which pathogenic bacteria may be most useful as the vaccine strains of the present invention. Using these additional criteria allows better selections to be made. In particular it has been found that, especially with pyrimidine pathway mutations, extracellular pathogenic bacteria are preferred for use in the present invention. This may be due to the difference in available pyrimidine levels outside the host cells, e.g., in serum, as opposed to pyrimidine levels inside the cells of the host.

In preparing the live vaccine strains, one generally introduces a marker for distinguishing the auxotrophic mutant to be produced from other members of the strain into the vaccine strain. Various marker genes can be employed, such as resistance to antibiotic or synthetic antibacterial drugs, a block in a biosynthetic pathway causing a requirement for an amino acid or the like. The limitation on the particular marker is that it should not affect the immunogenic character of the microorganism, nor should it interfere with the processing of the microorganism to produce the live vaccine strain. The marker gene will alter the phenotype to allow for recognition of the subject microorganism.

Preferred pathogenic bacteria for use in the present invention will have stable mutations with few reversions. Frequencies of reversions less than about $10^{-7}$ indicate stable mutations[38]. It has been found that many temperature sensitive mutants, especially those which are uncharacterized, which effect DNA synthesis may be unsuitable for use as live vaccine strains due to the high frequency of reversions found in these mutants.

The use of a transducing phage, DNA-mediated transformation, and/or conjugation may also be employed to successively produce two or more independently mutated genes in a single host strain to be used as the vaccine strain. The presence of two completely independent mutations, each of which has an extremely low probability of reversion, provides almost absolute assurance that the vaccine strain cannot become virulent. In addition, each gene chosen will be involved in at least one, and preferably at least two, of the cellular functions of the bacteria such that the microorganism will be unable to multiply sufficiently to cause disease.

This invention also provides vaccine strains of E. coli which contain one or more attenuating mutations. While a pyrimidine pathway mutation (such as the carAB mutation), an iron metabolism mutation (such as the fur mutation), or a colicin transport mutation (such as the tolC mutation) are preferred embodiments, attenuating mutations of E. coli useful in the present invention are not limited to these mutations. Other mutations of interest include mutations in the groELES operon, whose products function as chaperonins and assist in polypeptide folding and assembly; mutations in htr genes, which are required for growth at elevated temperatures but not at 30° C.; and mutations in the recA gene, which is involved in general recombination and DNA damage repair.

E. coli vaccine strains of this invention are prepared generally as follows. An E. coli strain carrying the desired mutation is grown overnight, incubated with P1 phage, then grown again overnight on selected media containing chloramphenicol. E. coli lysogenic for P1 are isolated. A lysate is prepared by heat shocking the cells, then using chloroform to facilitate lysis. After centrifugation, the lysate is incubated with the E. coli strain to be transduced, then plated on selective media and incubated overnight. Isolates are tested to confirm that they contained the desired phenotype.

DNA-mediated transformation and/or conjugation may also be employed to produce one or more desired attenuating mutations in an E. coli strain to be used as the vaccine strain. Alternatively, an E. coil strain to be used as the vaccine strain may be treated with a chemical mutagen, such as nitrosoguanidine, or irradiated, such as with x-rays and the resulting attenuated mutants isolated according to the characteristics desired. Useful spontaneous mutations may also be isolated. Other methods which may be useful for producing mutants include site-directed mutagenesis[26] and restriction enzyme digestion and religation.

As discussed previously, the subject vaccines may be used in a wide variety of vertebrates. The subject vaccines will find particular use with man, domestic animals or other animals.

The manner of application of a vaccine strain of this invention may be varied widely, any of the conventional methods for administering a live vaccine being applicable. These include aerosol applications, oral applications, in drinking water, on a solid physiologically acceptable base, or in a physiologically acceptable dispersion, parenterally (e.g., subcutaneously, intramuscularly, intravascularly, or intraperitoneally), by injection, by in ovo inoculation or the like. The dosage of the vaccine (number of bacteria, number of administrations, period of administration, etc.) will depend on route of administration and will vary according to the vaccine strain used and the species, age, and size of host to be protected. A person skilled in the art will be able to determine the dosage to be administered so as to provide a sufficient immune response.

The formulation of vaccine strain compositions may vary widely. Pharmaceutically acceptable vehicles, such as water, are expected to be useful for oral administration. Other pharmaceutically acceptable vehicles such as normal saline may be used for parenteral, cloacal or other routes of administration. The vaccine composition may also be admixed in the food for some applications.

The following examples are not intended to limit the scope of the invention in any manner.

EXAMPLES OF EMBODIMENTS OF THE INVENTION

In general, the following materials and methods were used in these examples unless otherwise noted.

(1) Animal Model for Colisepticemia:

In order to test the feasibility of oral vaccination and the efficacy of the live vaccine strains of this invention, it was essential to establish an experimental model of the disease. Since colisepticemia outbreaks in domestic fowl are often observed following hemorrhagic enteritis virus (HEV) infection, this model was based on challenge of $HEV_A$-infected birds with E. coli. Similar models have been used by others to study colisepticemia in domestic fowl[11,12].

Turkeys were obtained from Hybrid Turkeys, Inc., Kitchener, Ontario, Canada, as one-day-old poults. They were housed with access to water and turkey starter ration (Co-op Feeds) and treated in accordance with the guidelines established by the Canadian Council of Animal Care.

During challenge experiments, $HEV_A$ was delivered by oral administration to individual poults at seven weeks of age. The dose of $HEV_A$ used was 100 times the $ED_{95}$. The $ED_{95}$ was defined as the dose that produced $HEV_A$ antigen in the spleens in 95% of 6-week old birds. E. coli was administered by three routes: (1) intravenous injection via a wing vein, (2) direct injection into the air sac with a small gauge needle, or (3) intratracheal injection between the tracheal rings with a small gauge needle. Vaccination of poults with E. coli was carried out at four weeks of age by oral administration to individual birds or via drinking water. Following $HEV_A$ and E. coli challenge, birds were examined daily for clinical signs of disease (bloody diarrhea, inappetence, arthritis), and seven days after bacterial challenge, all birds were sacrificed by cervical dislocation. Post mortems were carried out. Organ samples were cultured for E. coli, and the identity of all isolates was confirmed by biochemical tests.

(2) Development of Mutants of E. coli:

E. coli of serotype 01 (EC222), 02 (EC317) and 078 (EC234) were used as host strains. EC234 (serotype 078:K80:H9) is a field isolate obtained from Dr. L. Arp at Iowa State University, U.S.A. EC222 (serotype 01:H nontypeable) was isolated from the liver of a chicken broiler and was obtained from the Animal Health Division of Alberta Agriculture, Canada. EC317 (serotype 02:non-motile) was obtained from a diseased turkey and was provided by Dr. C. Riddell at the Western College of Veterinary Medicine, Saskatoon, Saskatchewan, Canada.

The source of carAB mutation was E. coli CGSC6181 (originally called NK6034; in our collection EC322). It was obtained from the E. coli Genetic Stock Center, Yale University, U.S.A. It was originally produced by N. Kleckner. It is car96::Tn10, Δ(gpt-lac)5, relA1, spoT1, thi-1, λ-.

The source of the fur gene was E. coli EC399, which is BN4020, obtained from Dr. Neiland, University of California, Berkeley, U.S.A. It is his arg thi lac Δ U169 galK fur::Tn5($Kn^R$).

The source of the tolC gene was E. coli EC532, which is GC7459, obtained from Dr. A. Jaffé, Institut Jacques Monod, Centre National de la Recherche Scientifique, Université Paris 7, 2 Place Jussieu, 75251 Paris Cedex 05, France. It is tolC::Tn10.

Generalized transducing phage Plcml, clr100 was obtained from Cold Springs Harbor Laboratory or M. Theisen of Veterinary Infections Disease Organization, Saskatoon, Saskatchewan, Canada. It is a mutant of phage P1 that carries the genes for chloramphenicol resistance and is temperature sensitive. At 42° C. clear plaques are produced while at 30° C. turbid plaques are produced.

E. coli EC322, EC399, or EC532 was grown overnight at 37° C. in LB+5 mM $CaCl_2$. To 0.5 mL of E. coli 25 μL of P1 was added. After incubation at 30° C. for 30 minutes 100 μL of this mixture was spread on each LB plate containing 12.5 μL per mL of chloramphenicol. The plates were incubated at 30° C. overnight. Colonies that grew were checked to be sure the strain was now temperature sensitive. (Strains lysogenic for this phage should not grow at 42° C.) LB plates containing chloramphenicol were prewarmed to 43° C. and then inoculated with the strain that was putatively lysogenic for P1. To facilitate comparison with growth at 30° C. a single colony was suspended in normal saline, and 100 μL of this suspension was spread on a prewarmed plate (which was incubated at 42° C.) and on an unwarmed plate (which was incubated at 30° C.). After overnight incubation the growth on the plates was compared. Cultures that were temperature sensitive were stored at −70° C.

E. coli lysogenic for P1 was grown at 30° C. in LB+10 mM $MgSO_4$ overnight. A 1:200 dilution from this culture was made into the same medium (50 mL in a 500 mL flask). The culture was incubated at 30° C. with shaking until mid log phase (carAB) or an absorbance at $OD_{660}$ of 0.2 (fur and tolC) was reached. The culture was then shifted to 40° C. (carAB) or 42° C. (fur and tolC) and incubated for 40 minutes (carAB) or 20 minutes (fur and tolC) with aeration. The fur and tolC shift was done rapidly using a 42° C. water bath. The culture was then transferred to 37° C. and incubated for 1 to 2 hours. Partial lysis had occurred, and 5 mL of chloroform was added to facilitate lysis. After an additional 10 minutes at 37° C. the culture debris was removed by centrifugation (10,000 rpm for 10 min in SS34 rotor). The supernate was carefully transferred to a sterile screwtop tube containing 0.5 mL of chloroform. The lysate was stored at 4° C.

The strain to be transduced (EC234, EC222, EC317) was grown overnight in 5 mL of LB +5 mM $CaCl_2$ at 37° C. with shaking.

For carAB, equal volumes of phage lysate and cells were mixed. The phage lysate was either used undiluted or diluted ten times. The mixtures were incubated at 30° C. for 30 min and then plated on LB containing 5 or 10 μg/mL of tetracycline. The plates were incubated at 37° C. or 42° C. overnight. The bacterial colonies were picked and streaked on LB+tetracycline plates to check for purity.

For fur and tolC, the cells were pelleted by centrifugation and resuspended in the original volume of 100 mM $MgSO_4$ and 5 mM $CaCl_2$. The cells were aerated for 15 min at 37° C. Equal volumes of phage lysate and cells were mixed. The phage lysate was used either undiluted or diluted ten times. The mixtures were incubated at 30° C. for 30 min and then plated on LB containing 50 μg/mL of Kanamycin (fur) or LB containing 10 μg/mL of tetracycline (tolC). The plates were incubated at 37° C. overnight. A few large colonies were seen on each plate and also a few pinpoint colonies. The large bacterial colonies were picked and streaked on LB+Kanamycin plates (fur) or LB+tetracycline plates (tolC)

to check for purity. These cultures were stored at 4° C. until the phenotype could be confirmed.

These cultures were tested to confirm that they contained the correct (i.e., carAB, fur or tolC) phenotype.

To confirm the carAB phenotype, M9 salts agar (plus 0.2 or 0.5% casamino acids) was prepared and was supplemented with uracil (final concentration 20 μg/mL). M9 salts medium will not support the growth of cultures containing the carAB mutation but will support the growth of the avian isolates of *E. coli* used. Supplementation with uracil allows the growth of isolates containing the carAB mutation. Strains that grow well on M9 salts agar with uracil but do not grow on M9 salts medium are considered to be carAB. Alternatively, M9 salts medium containing 50 ng/mL nicotinic acid supplemented with uracil and arginine will support growth of bacteria containing carAB mutations, while the same medium without nicotinic acid will not support their growth.

To confirm the presence of the fur mutation, cultures were grown in LB or LB plus 200 μM 2,2'-dipyridyl (DIP) at 37° C. with shaking in 5 mL tubes for 20 hours. The absorbance at $OD_{660}$ was determined. The cells were pelleted using a bench top centrifuge and the pellet discarded. The supernates were stored at −20° C. until the assays were done. The method of Rioux et al.[40] was used to determine the catechol siderophores in the supernates. Results were expressed as an absorbance ratio of $OD_{510}/OD_{660}$. These ratios were compared to that of the control wildtype strain. When the ratio of the mutants grown in iron rich medium was higher than that of the wildtype, the strains were used for further testing using outer membrane preparations. For outer membrane preparations cells were grown with or without DIP in LB to an absorbance $OD_{660}$ of about 1 to 2. Culture volume was 100 mL. Cells were harvested by centrifugation, washed twice with normal saline and stored at −20° C. until used. Cells were resuspended in 5 mL Hepes buffer (10 mM, pH 7.4), transferred to a 15 mL tube and broken open by sonication. This material was transferred to a 37 mL tube (for the SS34 rotor) and centrifuged at 10,000 rpm for 10 minutes to remove debris. The supernate (usually 4 mL) was transferred to an oakridge tube for the type 50 rotor and 1.5 mL of 4% Sarkosyl (N-lauroylsarcosine, sodium salt) was added. This was incubated at room temperature for 30 min. The Sarkosyl insoluble fraction was pelleted by centrifuging in an ultracentrifuge for 1 hour, at 15° to 20° C. at 35,000 rpm. The supernate was discarded. The small and clear to slightly turbid pellet was resuspended in 5 mL of 2% Sarkosyl using a disposable loop. It was then incubated for 30 min at room temperature and recentrifuged in an ultracentrifuge for 1 hour at 15° to 20° C. at 35,000 rpm. This pellet was dissolved in 250 μL of Hepes buffer and stored at −20° C. until used. Proteins were separated by discontinuous sodium dodecyl sulfate-polyacrylamide gel electrophoresis (usually 10%) and stained with Coomassie brilliant blue. Mutants were identified as containing fur mutations based on their over production of catechols and iron-regulated outer membrane proteins in iron rich medium.

To confirm the tolC phenotype, isolates were selected for tetracycline resistance and inability to grow in LB containing 5 mg/mL of sodium dodecyl sulfate (SDS). Wildtype *E. coli* grow well in this concentration of SDS, while tolC mutants cannot[37].

Tetracycline sensitive derivatives were selected on medium containing chlortetracycline and fusaric acid (J. Bacteriol. 145:1110–1112, 1981). Tetracycline resistant carAB mutants were grown overnight in 5 mL of brain heart infusion (BHI) broth at 37° C. The cells were washed once with Minca medium and resuspended to an $OD_{660}$ of 0.05. Dilutions from $10^{-1}$ to $10^{-3}$ were made and 0.1 mL was plated per plate. Plates were incubated for 48 hours at 37° C. Large colonies were picked and streaked on BHI plates. The tetracycline sensitivity and presence of carAB mutation was confirmed.

Where noted, spontaneous rifampicin resistant mutants were selected before the tetracycline-sensitive derivatives were selected. This was done by streaking plates containing a gradient of rifampicin (from 50 to 100 μg/mL) with the carAB mutants and incubating at 37° C. overnight. Colonies that grew were checked to be sure that they were still tetracycline resistant and had the carAB phenotype.

Bacterial strains were stored at −70° C. in 25% glycerol and 50% BHI broth.

Vaccine strains prepared as previously described using virulent strains of *E. coli* which have been attenuated by insertion of carAB mutation from *E. coli* CGSC6181 and which are tetracycline resistant have been deposited with the American Type Culture Collection (ATCC). These strains are: (1) EC 645, ATCC Accession No. 55345, which is derived from EC 234 (serotype 078); (2) EC 644, ATCC Accession No. 55347, which is derived from EC 317 (serotype 02); and (3) EC 643, ATCC Accession No. 55349, which is derived from EC 222 (serotype 01).

Rifampicin resistant carAB mutants that are tetracycline resistant have been identified and isolated. These strains include: (1) EC749, which is derived from EC644 (serotype 02, carAB::Tn10 in EC317); (2) EC750, which is derived from BA4 (serotype 01, carAB::Tn10 in EC222); and (3) EC769, which is derived from EC645 (serotype 078, carAB::Tn10 in EC234).

Stable tetracycline sensitive rifampicin resistant carAB mutants have been isolated and identified. These strains include: (1) BA57 (EC752), which is derived from EC234 (serotype 078); (2) BA74, which is derived from EC234 (serotype 078); (3) BA83 (EC753), which is derived from EC234 (serotype 078); (4) BA95 (EC751) which is derived from EC317 (serotype 02, ATCC Accession No. 69402); (5) BA96 (EC754), which is derived from EC317 (serotype 02); (6) BA101 (EC755), which is derived from EC317 (serotype 02); (7) BA104, which is derived from EC222 (serotype 01); (8) BA105, which is derived from EC222 (serotype 01); and (9) BA108, which is derived from EC222 (serotype 01).

Several mutants were isolated and identified as containing the fur mutation based on their over production of catechols and iron-regulated outer membrane proteins in iron-rich medium. These strains include: (1) EC655, which is derived from EC317 (serotype 02); (2) EC656, which is derived from EC222 (serotype 01); (3) EC657, which is derived from EC222 (serotype 01); (4) EC658, which is derived from EC222 (serotype 01); (5) EC662, which is derived from EC234 (serotype 078); and (6) EC663, which is derived from EC234 (serotype 078).

Several mutants were isolated and identified as containing the tolC mutation based on their tetracycline resistance and their inability to grow in LB containing 5 mg/Ml of SDS. These strains include: (1) BA142, which is derived from EC317 (serotype 02); (2) BA143, which is derived from EC317 (serotype 02); (3) BA144, which is derived from EC222 (serotype 01); (4) BA145, which is derived from EC222 (serotype 01); (5) BA146, which is derived from EC234 (serotype 078); and (6) BA147, which is derived from EC234 (serotype 078).

EXAMPLE 1

Oral Delivery of *E. coli* Vaccines

As discussed previously, attenuated bacteria would be ideal for use in a vaccine which could be delivered in drinking water. The first step in this process was to test the feasibility of vaccinating poults with *E. coli* delivered orally.

Duplicate groups of 8 birds were immunized orally at four weeks of age with $5\times10^8$ colony forming units (CFU) of wildtype *E. coli* serotype 01 or 02 as shown in Table 1. All groups were housed in separate rooms, and four unimmunized poults were included in each room in order to determine if the *E. coli* could be transferred by shedding. After three weeks, poults were challenged with $HEV_A$ followed seven days later by $5\times10^{10}$ CFU of wildtype *E. coli* 01 or 02. The results, summarized in Table 1, indicate oral immunization with either serotype was effective in inducing protection against challenge with both serotypes. Therefore, only one of these two serotypes need be included in a vaccine formulation. Further, unvaccinated sentinel animals housed in the same rooms as vaccinated poults were protected, indicating that the *E. coli* could be spread by fecal shedding. A similar experiment was conducted with serotypes 02 and 078 (Table 2). In this case, no cross-protection was observed indicating that both of the serotypes should be present in a vaccine to provide broad-spectrum protection.

TABLE 1

Oral immunization of turkeys with *E. coli* serotypes 01 and 02.

| Group[3] | Number of Poults | Immunizing Strain | Challenge Strain | Mortality | Morbidity[1] & Mortality |
|---|---|---|---|---|---|
| A1 | 8 | 01 | 01 | 0 | 1 |
| A2 | 4 | ND[2] | 01 | 0 | 0 |
| B1 | 8 | 01 | 02 | 0 | 0 |
| B2 | 4 | ND[2] | 02 | 0 | 2 |
| C1 | 8 | 02 | 01 | 0 | 2 |
| C2 | 4 | ND[2] | 01 | 0 | 2 |
| D1 | 8 | 02 | 02 | 0 | 0 |
| D2 | 4 | ND[2] | 02 | 0 | 0 |
| E | 12 | None | 01 | 6 | 8 |
| F | 12 | None | 02 | 4 | 6 |
| G | 12 | None | None | 0 | ND[2] |

[1]Morbidity = birds with *E. coli* lesions at post mortem.
[2]ND = not done
[3]Groups with same letter were housed in the same room.

TABLE 2

Oral immunization of turkeys with *E. coli* serotypes 02 and 078.

| Group[1] | Number of Poults | Immunizing Strain | Challenge Strain | Mortality | Morbidity[2] & Mortality |
|---|---|---|---|---|---|
| A1 | 8 | 078 | 02 | 6 | 6 |
| A2 | 4 | None | 02 | 2 | 2 |
| B1 | 8 | 078 | 078 | 0 | 0 |
| B2 | 4 | None | 078 | 0 | 1 |
| C1 | 8 | 02 | 02 | 0 | 1 |
| C2 | 4 | None | 02 | 0 | 0 |
| D1 | 8 | 02 | 078 | 2 | 4 |
| D2 | 4 | None | 078 | 3 | 3 |
| E | 8 | None | None | 3 | 5 |
| F | 8 | None | None | 0 | 3 |
| G | 12 | None | None | 0 | 0 |

[1]Groups with the same were letter were housed in the same room.
[2]Morbidity = birds with *E. coli* lesions at post mortem.

EXAMPLE 2

Attenuation of *E. coli* serotype 01 and 078 using carAB mutation.

Since oral immunization of poults with live *E. coli* appeared to be feasible, the attenuation of serotype 01 and 078 strains was initiated. Mutations in the carAB operon resulted in strains which required arginine plus uracil for growth. *E. coli* laboratory strains carrying the drug-resistant transposon Tn10 (tetracycline resistance) insertions in this operon were used as the source of the mutations. They were transferred into serotypes 01 and 078 by transduction, and the Tn10 sequence was eliminated. Details of the procedures used were previously discussed in (2) Development of Mutants of *E. coli*. These strains were then tested for virulence using one-day-old chickens. Day old chicks are known to be susceptible to challenge with wildtype *E. coli*. The results for five carAB mutants are listed in Table 3. The dose of bacteria in this experiment was $5\times10^4$ CFU. Since the $LD_{50}$ of the serotype 01 strain EC 222 is $1\times10^2$ CFU, the carAB mutation had attenuated these strains significantly. This experiment was repeated once again with results similar to those described above.

TABLE 3

Virulence of carAB mutants of serotypes 01 and 078 in a young chick model.

| | | Mortality by day | | | | | | | |
|---|---|---|---|---|---|---|---|---|---|
| Strain[1] | Serotype | 1 | 2 | 3 | 4 | 5 | 6 | 7 | Total Mortality[2] |
| — | — | 0 | 0 | 0 | 0 | 0 | 0 | 0 | 0 |
| EC222 (boiled) | 01 | 0 | 0 | 0 | 0 | 0 | 0 | 0 | 0 |
| BA103 | 01 | 0 | 0 | 0 | 0 | 1 | 1 | 0 | 2 |
| BA104 | 01 | 0 | 2 | 2 | 0 | 0 | 0 | 0 | 4 |
| BA105 | 01 | 2 | 0 | 0 | 1 | 2 | 0 | 0 | 5 |
| EC222 | 01 | 9 | 0 | 0 | 1 | 0 | 0 | 0 | 10 |
| BA74 | 078 | 0 | 0 | 0 | 1 | 0 | 0 | 0 | 1 |
| BA73 | 078 | 0 | 0 | 0 | 0 | 0 | 0 | 0 | 0 |
| EC234 | 078 | 1 | 0 | 0 | 2 | 2 | 3 | 1 | 9 |

[1]Strains with the prefix "EC" are field isolates; BA103, BA104 and BA105 are carAB mutants derived from EC222; and BA74 and BA73 are carAB mutants derived from EC234.
[2]Total number of birds per group = 10.

EXAMPLE 3

Immunization with CarAB Mutants of *E. coli* Serotype 078

An experiment was conducted to determine if carAB mutant strains of *E. coli* were capable of providing protection from challenge with the wildtype strain. Turkeys were immunized orally with $5\times10^9$ cfu of bacteria when 4 weeks old, then challenged with the standard challenge model of $HEV_A$ at 6 weeks of age followed by the wildtype bacteria intratracheally at 7 weeks of age.

Birds in Group A were immunized with wildtype *E. coli* serotype 078. Group B received *E. coli* serotype 078 with carAB mutation. Group C was immunized with *E. coli* serotype 078 with carAB and rifampicin mutations. Birds in Group D were not immunized.

Results are presented in Table 4. All birds in Groups A, B, and C remained healthy. No lesions were observed post mortem. Six of the 8 birds in control Group D died within 4 days of challenge. These results show that high doses of the mutant strains of *E. coli* serotype 078 used provided an effective protection against challenge with the wildtype strain.

TABLE 4

Oral immunization of turkeys with *E. coli* serotype 078.

| Group | Number of Poults | Immunizing Strain | Challenge Strain | Mortality | Morbidity & Mortality |
|---|---|---|---|---|---|
| A | 8 | 078 | 078 | 0 | 0 |
| B | 8 | 078 [carAB] | 078 | 0 | 0 |
| C | 8 | 078 [carAB + Rif®] | 07& | 0 | 0 |
| D | 8 | None | 078 | 6 | 6 |

EXAMPLE 4

Attenuation of *E. coli* serotype 01 using fur mutation.

Details of the procedures used to produce fur mutants were previously discussed in (2) Development of Mutants of *E. coli*.

Two strains (EC656 and EC657) were tested for virulence using the young chick model. The results for these two fur mutants are shown in Table 5. Newborn chicks were obtained from a local hatchery. These birds were divided into 6 groups of 20 and housed separately. On Day 0 each group of chickens was challenged with 0.25 mL of bacteria (containing about $10^4$ cfu or $10^2$ cfu—see Table 5 for exact dose). The challenge was given as a subcutaneous injection of 0.25 mL. The usual precautions were taken to prevent cross contamination during administration of the challenge. The chicks were monitored for mortality at 6 hours post challenge and then every 12 hours for 7 days. After 7 days the remaining birds were sacrificed.

Since the mortality of the group receiving serotype 01 wildtype after 3 and 7 days was 55 and 80%, respectively ($8\times10^2$ cfu's, low dose), and 100% after 3 days ($8\times10^4$ cfu's, high dose), the fur mutation had attenuated these strains significantly.

EXAMPLE 5

Attenuation of *E. coli* serotype 02 using tolC mutation.

Details of the procedures used to produce tolC mutants were previously discussed in (2) Development of Mutants of *E. coli*. Two strains (BA 142 and BA 143) were tested for virulence using the young chick model described in Example 4. A carAB mutant strain (BA95) was also used as an attenuated control. All birds received $1\times10^4$ cfu's of bacteria. The results are shown in Table 6. Since the total birds affected in the group receiving serotype 02 wildtype was 50%, the tolC mutation had attenuated strain BA 142 significantly. Strain BA 143 did not appear to be attenuated in this test.

TABLE 6

Virulence of tolC mutants of serotype 02 in a young chick model.

| STRAIN | MORTALITY AFTER 7 DAYS | LESIONS AFTER 7 DAYS | TOTAL BIRDS AFFECTED | PHENOTYPE |
|---|---|---|---|---|
| NONE | 0/12 | 0/12 | 0/12 | — |
| BA142 | 2/20 | 2/18 | 4/20 | tolC |
| BA143 | 6/19 | 3/13 | 9/19 | tolC |
| BA95 (EC751) | 2/20 | 1/18 | 3/20 | carAB |
| EC317 | 7/20 | 3/13 | 10/20 | wildtype |

EXAMPLE 6

Attenuation of *E. coli* serotype 02 using carAB mutation.

Details of the procedures used to produce carAB mutants were previously discussed in (2) Development of Mutants of *E. coli*. Strain BA95 was tested for virulence using the young chick model described in Example 4. All birds received about $5\times10^4$ cfu's bacteria by subcutaneous injection. The LD$_{50}$ of wildtype EC317 (serotype 02) is $6\times10^2$ cfu's. Results are shown in Table 7. The carAB mutation had attenuated strains BA95, BA96, and BA101 significantly. All three strains are tetracycline sensitive, rifampicin resistant carAB mutants derived from EC317 (serotype 02).

TABLE 5

Virulence of fur Mutants by Serotype 01 in a Young Chick Model.

| Group[1] | day 0 | day 1 | day 2 | day 3 | day 4 | day 5 | day 6 | day 7 | Total Mortality | Dose[2] |
|---|---|---|---|---|---|---|---|---|---|---|
| BHI | 1* | 0 | 0 | 0 | 0 | 0 | 0 | 0 | 1/13 | — |
| EC656 | 0 | 0 | 0 | 0 | 0 | 0 | 0 | 0 | 0/20 | low |
| EC656 | 0 | 0 | 0 | 0 | 0 | 0 | 0 | 1 | 1/20 | high |
| EC657 | 0 | 0 | 1 | 0 | 2 | 0 | 0 | 0 | 3/20 | low |
| EC657 | 0 | 0 | 0 | 1 | 0 | 0 | 0 | 0 | 1/20 | high |
| EC222 | 0 | 10 | 0 | 2 | 3 | 0 | 2 | 0 | 17/20 | low |
| EC222 | 0 | 17 | 1 | 0 | 0 | 0 | 0 | 0 | 18/20 | high |

*This bird was not healthy before challenge.
[1]EC656 and EC657 are fur mutants derived from EC222 (serotype 01).
[2]Doses were as follows:
EC222, low dose $8 \times 10^2$ cfu's
high dose $8 \times 10^4$ cfu's
EC656, low dose $7 \times 10^2$ cfu's
high dose $7 \times 10^4$ cfu's
EC657, low dose $5 \times 10^2$ cfu's
high dose $5 \times 10^4$ cfu's

TABLE 7

Virulence of carAB mutants of serotype O2 in a young chick model.

| CHALLENGE | MORTALITY AFTER DAY 3 | MORTALITY AFTER DAY 7 |
|---|---|---|
| NONE | 0/21 | 0/21 |
| WILDTYPE (EC317) | 20/20 | 20/20 |
| MUTANT (BA95) | 1/21 | 3/21 |
| MUTANT (BA96) | 0/21 | 1/21 |
| MUTANT (BA101) | 2/21 | 2/21 |

EXAMPLE 7

Immunization with carAB Mutants of *E. coli* serotype O2.

An experiment was conducted to determine if carAB mutant strains of *E. coli* were capable of providing protection from challenge with the wildtype strain. Turkeys were immunized orally with $5 \times 10^8$ cfu of bacteria when 4 weeks old, then challenged with the standard challenge model of $HEV_A$ at 6 weeks of age to render the birds susceptible to *E. coli*. This was followed by challenge with $5 \times 10^8$ cfu's of the wildtype bacteria in 0.2 ml, administered intratracheally at 7 weeks of age.

Birds in Group C were immunized with wildtype *E. coli* serotype O2. Group B received *E. coli* serotype O2 with carAB mutation. Birds in Group A were not immunized.

Results are presented in Table 8. All birds in Groups B and C remained healthy. No lesions were observed post mortem. Two of the 10 birds in control Group A died within 7 days of challenge; seven of the 10 birds in control Group A showed morbidity and/or mortality. These results show that high doses of the mutant strains of *E. coli* serotype O2 used provided an effective protection against challenge with the wildtype strain.

TABLE 8

Oral immunization of Turkeys with *E. coli* serotype O2.

| GROUP | VACCINE STRAIN | CHALLENGE & STRAIN | MORTA-LITY | MORBIDITY & MORTALITY |
|---|---|---|---|---|
| A | NO VACCINE | EC317 | 2/10 | 7/10 |
| B | MUTANT (BA95) | EC317 | 0/9 | 0/9 |
| C | WILDTYPE (EC317) | EC317 | 0/10 | 0/10 |

EXAMPLE 8

Screening for stability of *E. coli* carAB mutants.

Preliminary testing was performed as follows:

Sixty-eight bacterial strains with carAB mutations were grown overnight in BHI broth at 37° C. with shaking.

Cells were washed twice in normal saline and concentrated 10 times, then 0.1 mL of the preparation containing approximately $10^9$ bacteria was placed on M9 medium containing 50 ng/mL nicotinic acid and incubated at 37° C. for 48 hours. Duplicate plates were made for each mutant strain. Since two of the wildtype strains required nicotinic acid for growth, it was included in 20 the minimal medium in vitro. The 33 strains that showed no growth on these plates, i.e., had not exhibited reversion to wildtype, were selected for secondary screening.

Secondary screening for stability of the carAB mutants was performed as follows: the 33 strains were grown in L broth (5 Ml in test tube) at 37° C. overnight with shaking. The culture was diluted 10:100 mL of BHI broth and grown overnight under the same conditions. This step was repeated; then 50 mL of culture was pelleted and washed twice with normal saline. The final pellet was suspended in 1 mL of saline (a 50× concentration); then 0.1 mL of the concentrate containing approximately $10^{11}$ cfu's was spread on each of two M9 minimal agar plates which had been supplemented with nicotinic acid. Plates were incubated for 48 hours at 37° C. and examined for growth at 24 and 48 hours. Nine of the 33 strains screened showed no reversions.

Secondary screening was repeated one or two additional times on the nine strains that had no growth in the first secondary screening. Results are shown in Table 9. Reversion frequency was calculated as total number of revertants divided by the total number of cfu's plated. These data show that *E. coli* carAB mutations are stable, with reversion frequencies less than $1 \times 10^{-9}$.

TABLE 9

Reversion frequencies of carAB mutants.

| STRAIN | SERO-GROUP | Total No. of Revertants - Trial 1[A] | Total No. of Revertants - Trial 2[A] | Total No. of Revertants - Trial 3[A] | Reversion Frequency[B] |
|---|---|---|---|---|---|
| BA57 (EC752) | 078 | 0 | ND | 0 | $<10^{-10}$ |
| BA74 | 078 | 0 | 17 | 26 | $4 \times 10^{-10}$ |
| BA83 (EC753) | 078 | 0 | 0 | 0 | $<10^{-11}$ |
| BA95 (EC751) | 02 | 0 | ND | 0 | $<10^{-10}$ |
| BA96 (EC754) | 02 | 0 | 0 | 1 | $1 \times 10^{-11}$ |
| BA101 (EC755) | 02 | 0 | 2 | 0 | $2 \times 10^{-11}$ |
| BA104 | 01 | 0 | 54 | 1 | $6 \times 10^{-10}$ |
| BA105 | 01 | 0 | 5 | 16 | $2 \times 10^{-10}$ |
| BA108 | 01 | 0 | 3 | 4 | $7 \times 10^{-11}$ |

[A]Total number of revertants on two plates. Each plate received $1.8 \times 10^{10}$ cfu's.
[B]Reversion frequency is expressed as total number of revertants divided by the total number of cfu's plated in all trials.

EXAMPLE 9

Growth of carAB mutants in turkey sera

Sera was collected from turkeys that had not been immunized. It was stored frozen until used. The sera was heated at 56° C. for 30 min to inactivate the complement. It was then centrifuged for 5 minutes in an eppendorf centrifuge to remove the particulate matter and filter sterilized.

Bacterial strains were grown overnight with shaking at 37° C. in BHI (5 ml in a 15 ml test tube); then 0.1 ml of overnight culture was transferred to 5 mL of BHI in a 15 ml test tube and grown for 3 hours at 37° C. with shaking. The cells were washed two times with normal saline and resuspended in 5 ml of normal saline. The absorbance at $OD_{660}$ nm was read to determine the cell density, and the bacteria were diluted with normal saline to give a concentration of approximately $10^6$ cfu's/mL.

All carAB mutants used had been tested for stability as described in Example 8. The carAB mutants were derived from the wildtype strain of the same serotype. The bacterial strains used are set forth in Table 10.

The bacteria were grown in turkey sera using the following procedures: 0.2 ml of the diluted cell suspension was added to 0.4 ml of sera and incubated at 37° C. Samples were taken at 0, 1.5, 3, and 6 hours of incubation. Dilutions were made in normal saline, and 0.025 ml volumes of several dilutions were spotted onto a BHI agar plate. The number of colonies was counted after 18 hours incubation at 37° C.

All strains tested grew in normal serum at approximately the same rate. These data indicate that carAB mutants are capable of growth in normal serum. This is unexpected in view of previous work which teaches that pyrimidine levels in serum may be limiting[41].

TABLE 10

Bacterial strains grown in turkey sera.

| STRAIN | SEROGROUP | PHENOTYPE |
|---|---|---|
| EC222 | 01 | WILDTYPE |
| EC234 | 078 | WILDTYPE |
| EC317 | 02 | WILDTYPE |
| BA74 | 078 | carAB mutant |
| BA83 (EC753) | 078 | carAB mutant |
| BA95 (EC751) | 02 | carAB mutant |
| BA96 (EC754) | 02 | carAB mutant |
| BA104 | 01 | carAB mutant |
| BA105 | 01 | carAB mutant |

EXAMPLE 10

Mapping Tn10 carAB junctions.

Localization of Tn10 by southern blot analysis was performed as follows: chromosomal DNA was isolated from EC317, EC222, EC234, EC749, EC750, and EC769 using the method of Stauffer et al. (Gene 14:63-72, 1981).

Plasmid pLLK12 was digested with PvuII and the fragments separated on agarose gels. DNA fragments were isolated from the agarose gel using GeneClean Kit (Bio 101 Inc. Box 2284, La Jolla, Calif., U.S.A.) according to the manufacturer's instructions. Fragments B & C were not well resolved on the gel so were used to produce a single probe. The probe specific for Tn10 was produced by digesting a plasmid containing Tn10 with BglII. DNA was labelled using the Oligolabelling kit (Pharmacia LKB Biotechnology) with [α-$^{32}$P]dCTP. Southern blot analysis was done according to standard techniques (Sambrook et al., 1989).

Tn10 was found to be inserted in the PvuII-E fragment of the carAB operon. The southern blot analysis of the PvuII digests of chromosomal DNA from insertion mutant EC749 produced an identical pattern when the BglII fragment of Tn10 containing the tetracycline resistance gene or the PvuIIE fragment of the carAB operon from pLLK12 was used as a probe. Probing chromosomal digests with either the fragment D or a mixture of fragments B & C produced dramatically different patterns.

The transposon appeared to be inserted at the same site in all three strains where the carAB::Tn10 was transferred to the cells by transduction with P1.

However, it is evident that there is restriction length polymorphism of the PvuII digested carAB operon in the wildtype strains EC222, EC317, and EC234, as a diversity of patterns was observed when the PvuII digested chromosomal DNA was probed with the carAB fragment E.

The carAB operon was cloned as follows: DNA from EC750 was used. This strain was produced by transducing the carAB operon marked with Tn10 from EC322 into EC222 as described earlier.

Chromosomal DNA was isolated from EC750 using the method of Stauffer et al. (Gene 14:63-72, 1981). The chromosomal DNA was digested with PvuII and ligated into the HincII site of pUC19 using the technique of Sambrook et al[27].

Subcloning efficiency competent E. coli DH5α (Gibco BRL Life Technologies, Inc., Gaithersburg, Md., U.S.A.) was transformed using 1-3 microliters (μL) of the ligation mix according to the manufacturer's instructions, and transformants were selected on plates containing 50 μg ampicillin. Clones that were also resistant to tetracycline were selected by replica plating on plates containing tetracycline. A plasmid with the reading frame of the carAB operon in the same orientation as the vector (pJK931) was selected for further study. The strain containing pJK931 is EC745.

Sequence analysis was performed as follows: using synthetic primers the sequence for both strands of DNA was obtained. Since the sequence of both Tn10 and the carAB operon are known[18,42,43] it was possible to determine the exact site of insertion of Tn10 into the operon. The transposon T 10 was inserted into the operon at the 5'-GGCTTTGCC-3', nucleotides 3139 to 3147 of carAB[18]. The Tn10 insertion involves recognition, cleavage, and duplication of a specific nine base pair (bp) target consensus sequence, 5'-NGCTNAGCN-3'[44]. Comparison of the carAB target site with the putative consensus sequence reveals a difference only at position 6 where A is replaced by T. However, the six consensus base pairs comprising the interrupted three bp inverted symmetry is preserved.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed is:

1. A vaccine strain of E. coli, wherein said vaccine strain is an attenuated virulent strain of E. coli comprising a fur mutation, said mutation providing attenuation of the virulence of said E. coli strain, wherein said strain retains its immunogenic properties so as to be protectively immunogenic.

2. A vaccine strain as in claim 1 wherein the vaccine strain is a live vaccine strain.

3. A vaccine strain as in claim 1 wherein said strain has a reversion frequency of from 0 to about $10^{-7}$.

4. A vaccine strain as in claim 1 wherein said E. coli comprises an extracellular E. coli.

5. A vaccine strain as in claim 1 wherein said virulent strain of E. coli is selected from the group consisting of serotype 01, 02 and 078.

6. The vaccine strain of claim 1 further comprising a colicin transport mutation.

7. The vaccine strain of claim 6 wherein the colicin transport mutation is tolC.

8. A method of preparing a vaccine strain of E. coli comprising:

(a) selecting a virulent stain of E. coli;

(b) producing a fur mutation in said virulent strain of E. coli to provide an attenuated organism;

(c) isolating the attenuated E. coli which contains said fur mutation; and

21

(d) selecting said isolated *E. coli* wherein said selected *E. coli* retains its immunogenic properties so as to be protectively immunogenic.

9. The method of claim 10 wherein said vaccine strain has a reversion frequency of of from 0 to about $10^{-7}$.

10. The method of claim 8 comprising selecting an attenuating mutation associated with a marker gene.

11. The method of claim 10 wherein said marker gene is an antibiotic resistance gene.

12. The method of claim 10, further comprising isolating *E. coli* mutants which revert to antibiotic sensitivity.

13. The method of claim 8 further comprising producing a colicin transport mutation in said virulent strain.

14. The method of claim 13 wherein the colicin transport mutation is tolC.

15. A vaccine composition comprising in a pharmaceutically acceptable vehicle at least one *E. coli* strain, wherein said *E. coli* strain is an attenuated virulent *E. coli* strain comprising a fur mutation, said mutation providing attenuation of the virulence of said *E. coli* strain, wherein said strain retains its immunogenic properties so as to be protectively immunogenic.

16. The composition of claim 15 wherein said attenuated virulent *E. coli* strain is a live strain.

17. The composition of claim 15 which comprises at least two attenuated virulent strains of *E. coli*.

18. The vaccine composition of claim 15 where the *E. coli* strain further comprises a colicin transport mutation.

19. The vaccine composition of claim 18 wherein the colicin transport mutation is tolC.

20. A method of preventing colisepticemia in an animal comprising administering to said animal an effective amount of at least one vaccine strain of *E. coli* which causes said colisepticemia wherein said vaccine strain is an attenuated virulent strain of *E. coli* comprising a fur mutation said mutation providing attenuation of the virulence of said *E. coli* strain, wherein said strain retains its immunogenic properties so as to be protectively immunogenic.

21. The method of claim 20 wherein said administration is oral.

22. The method of claim 20 wherein said administration is to an avian species.

23. The method of claim 20 wherein at least two vaccine strains are administered.

24. The method of claim 20 further comprising producing a colicin transport mutation in said virulent strain.

25. The method of claim 24 wherein the colicin transport mutation is tolC.

26. A vaccine strain of *E. coli* wherein said vaccine strain is an attenuated virulent strain of *E. coli* comprising a fir mutation and a pyrimidine pathway mutation, said mutations providing attenuation of the virulence of said *E. coli* strain and wherein said strain retains its immunogenic properties so as to be protectively immunogenic.

27. The vaccine strain of claim 26 wherein the pyrimidine pathway mutation is carAB.

28. The vaccine strain of claim 26 further comprising a colicin transport mutation.

29. The vaccine strain of claim 28 wherein the colicin transport mutation is tolC.

30. A vaccine strain as in claim 26 wherein the vaccine strain is a live vaccine strain.

31. A vaccine strain as in claim 26 wherein said strain has a reversion frequency of from 0 to about $10^{-1}$.

32. A vaccine strain as in claim 26 wherein said *E. coli* comprises an extracellular *E. coli*.

33. A vaccine strain as in claim 26 wherein said virulent strain of *E. coli* is selected from the group consisting of serotype 01, 02 and 078.

22

34. A method of preparing a vaccine strain of *E. coli* comprising:
(a) selecting a virulent strain of *E. coli*;
(b) producing a fur mutation and a pyrimidine pathway mutation in said virulent strain of *E. coli* to provide an attenuated organism;
(c) isolating the attenuated *E. coli* which contains said fur mutation and said pyrimidine pathway mutation; and
(d) selecting said isolated *E. coli* wherein said selected *E. coli* retains its immunogenic properties so as to be protectively immunogenic.

35. The method of claim 34 wherein the pyrimidine pathway mutation is carAB.

36. The method of claim 34 further comprising producing a colicin transport mutation in said virulent strain.

37. The method of claim 36 wherein the colicin transport mutation is tolC.

38. The method of claim 34 wherein said vaccine strain has a reversion frequency of from 0 to about $10^{-7}$.

39. The method of claim 34 comprising selecting an attenuating mutation associated with a marker gene.

40. The method of claim 39 wherein said marker gene is an antibiotic resistance gene.

41. The method of claim 40 further comprising isolating *E. coli* mutants which revert to antibiotic sensitivity.

42. A vaccine composition comprising in a pharmaceutically acceptable vehicle at least one *E. coli* strain, wherein said *E. coli* strain is an attenuated virulent *E. coli* strain comprising a fur mutation and a pyrimidine pathway mutation, said mutations providing attenuation of the virulence of said *E. coli* strain, wherein said strain retains its immunogenic properties so as to be protectively immunogenic.

43. The vaccine composition of claim 42 wherein the pyrimidine pathway mutation is carAB.

44. The vaccine composition of claim 42 where the *E. coli* strain further comprises a colicin transport mutation.

45. The vaccine composition of claim 44 wherein the colicin transport mutation is tolC.

46. The composition of claim 42 wherein said attenuated virulent *E. coli* strain is a live strain.

47. The composition of claim 42 which comprises at least two attenuated virulent strains of *E. coli*.

48. A method of preventing colisepticemia in an animal comprising administering to said animal an effective amount of at least one vaccine strain of *E. coli* which causes said colisepticemia wherein said vaccine stain is an attenuated virulent strain of *E. coli* comprising a fur mutation and a pyrimidine pathway mutation, said mutations providing attenuation of the virulence of said *E. coli* strain, wherein said strain retains its immunogenic properties so as to be protectively immunogenic.

49. The method of claim 48 wherein the pyrimidine pathway mutation is carAB.

50. The method of claim 48 wherein said virulent strain of *E. coli* further comprises a colicin transport mutation.

51. The method of claim 50 wherein the colicin transport mutation is tolC.

52. The method of claim 48 wherein said administration is oral.

53. The method of claim 48 wherein said administration is to an avian species.

54. The method of claim 48 wherein at least two vaccine strains are administered.

55. A vaccine strain of *E. coli* wherein said vaccine strain is an attenuated virulent strain of *E. coli* comprising a pyrimidine pathway mutation, said mutation providing attenuation of the virulence of said *E. coli* strain and wherein said strain retains its immunogenic properties so as to be protectively immunogenic.

56. The vaccine strain of claim 55 wherein the pyrimidine pathway mutation is carAB.

57. The vaccine strain of claim 55 further comprising a colicin transport mutation.

58. The vaccine strain of claim wherein the colicin transport mutation is tolC.

59. A vaccine strain as in claim 55 wherein the vaccine strain is a live vaccine strain.

60. A vaccine strain as in claim 55 wherein said strain has a reversion frequency of from U to about $10^{-7}$.

61. A vaccine strain as in claim 55 wherein said *E. coli* comprises an extracellular *E coli*.

62. A vaccine strain as in claim 55 wherein said virulent strain of *E. coli* is selected from the group consisting of serotype 01, 02 and 078.

63. A method of preparing a vaccine strain of *E. coli* comprising:
    (a) selecting a virulent strain of *E. coli*;
    (b) producing a pyrimidine pathway mutation in said virulent strain of *E. coli* to provide an attenuated organism;
    (c) isolating the attenuated *E. coli* which contains said pyrimidine pathway mutation, and
    (d) selecting said isolated *E. coli* wherein said selected *E. coli* retains its immunogenic properties so as to be protectively immunogenic.

64. The method of claim 63 wherein the pyrimidine pathway mutation is carAB.

65. The method of claim 63 further comprising producing a colicin transport mutation in said virulent strain.

66. The method of claim 65 wherein the colicin transport mutation is tolC.

67. The method of claim 63 wherein said vaccine strain has a reversion frequency of from 0 to about $10^{-7}$.

68. The method of claim 63 comprising selecting an attenuating mutation associated with a marker gene.

69. The method of claim 68 wherein said marker gene is an antibiotic resistance gene.

70. The method of claim 69 further comprising isolating *E. coli* mutants which revert to antibiotic sensitivity.

71. A vaccine composition comprising in a pharmaceutically acceptable vehicle at least one *E. coli* strain, wherein said *E. coli* strain is an attenuated virulent *E. coli* strain comprising a pyrimidine pathway mutation, said mutation providing attenuation of the virulence of said *E. coli* strain, wherein said strain retains its immunogenic properties so as to be protectively immunogenic.

72. The vaccine composition of claim 71 wherein the pyrimidine pathway mutation is carAB.

73. The vaccine composition of claim 71 where the *E. coli* strain further comprises a colicin transport mutation.

74. The vaccine composition of claim 73 wherein the colicin transport mutation is tolC.

75. The composition of claim 71 wherein said attenuated virulent *E. coli* strain is a live strain.

76. The composition of claim 71 which comprises at least two attenuated virulent strains of *E. coli*.

77. A method of preventing colisepticemia in an animal comprising administering to said animal an effective amount of at least one vaccine strain of *E. coli* which causes said colisepticemia wherein said vaccine strain is an attenuated virulent strain of *E. coli* comprising a pyrimidine pathway mutation, said mutation providing attenuation of the virulence of said *E. coli* strain, wherein said strain retains its immunogenic properties so as to be protectively immunogenic.

78. The method of claim 77 wherein the pyrimidine pathway mutation is carAB.

79. The method of claim 77 wherein said virulent strain of *E. coli* further comprises a colicin transport mutation.

80. The method of claim 79 wherein the colicin transport mutation is tolC.

81. The method of claim 77 therein said administration is oral.

82. The method of claim 77 wherein said administration is to an avian species.

83. The method of claim 77 wherein at least two vaccine strains are administered.

* * * * *